United States Patent [19]

Merkl

[11] 4,017,527

[45] Apr. 12, 1977

[54] METALLIC-ORGANO-PEROXIDE AND ORGANO-METALLIC-PEROXIDE

[76] Inventor: George G. Merkl, 46 Sunset Court, Haworth, N.J. 07641

[22] Filed: Oct. 15, 1974

[21] Appl. No.: 514,681

Related U.S. Application Data

[62] Division of Ser. No. 319,293, Dec. 29, 1972, Pat. No. 3,969,387.

[52] U.S. Cl. .................................. 260/448 AD
[51] Int. Cl.$^2$ ................................ C07F 5/06
[58] Field of Search ........ 260/448 AD, 212, 231 A, 260/231 CM

[56] References Cited

UNITED STATES PATENTS

| | | | |
|---|---|---|---|
| 1,630,593 | 5/1927 | Young | 260/448 AD |
| 1,793,935 | 2/1931 | Kaufler et al. | 260/448 AD |
| 1,870,859 | 8/1932 | Maximoff | 260/448 AD |
| 2,292,205 | 8/1942 | Denison et al. | 260/448 AD |
| 2,579,251 | 12/1951 | Coates et al. | 260/448 AD |
| 2,666,076 | 1/1954 | Rex et al. | 260/448 AD |
| 2,927,124 | 3/1960 | Olmsted et al. | 260/448 AD |
| 3,446,828 | 5/1969 | Buzas et al. | 260/448 AD |
| 3,629,229 | 12/1971 | Schmank | 260/448 R |
| 3,856,841 | 12/1974 | Merkl | 260/448 AD |

*Primary Examiner*—Helen M. S. Sneed
*Attorney, Agent, or Firm*—Arnold, White & Durkee

[57] ABSTRACT

Peroxy compounds are prepared by contacting and reacting
  a. a reactive aluminum comprising highly pure aluminum permeated with a metal having an atomic volume close to hydrogen, e.g., a liquid metal selected from mercury, gallium and indium/gallium alloys with
  b. a liquid mixture of
    i. hydrogen peroxide, and
    ii. a member selected from alcohols, ketones, aldehydes and carboxylic acid esters.

The peroxy compounds formed are useful in detergents, cosmetics, food products and as catalysts.

21 Claims, No Drawings

METALLIC-ORGANO-PEROXIDE AND ORGANO-METALLIC-PEROXIDE

CROSS-REFERENCE TO RELATED APPLICATIONS

This application is a divisional of application Ser. No. 319,293, filed Dec. 29, 1972 now U.S. Pat. No. 3,969,387.

BACKGROUND OF THE INVENTION

The present invention relates to a method for the formation of metallic-organo-peroxides and organo-metallic peroxides and to such compounds so produced.

Many methods for forming organo-peroxides are known. Reference is made to the book, "Hydrogen Peroxide in Organic Chemistry" by John G. Wallace, published by the Electro Chemical Department of Eldu Pont De Neumours and Company.

Generally, an organic peroxide is defined as a derivative formed by replacing one or both hydrogen atoms of hydrogen peroxide by an organic radical. The present method produces compounds which include a metal atom bonded to an organic radical and a peroxide type bonded to the organic radical. The peroxide group is the oxygen to oxygen type bond is which a hydrogen atom can be connected to one of the oxygen atoms. The method of the present invention also produces a product wherein the organic radical has a metallic atom bonded to it and the peroxide group is bonded to the metal atom. The differences in the types of products produced gives rise to the distinction between the description of the product as being on the one hand a, metallic-organo-peroxide and on the other hand an, organo-metallic-peroxides.

One elementary method of producing an organic peroxide makes use of the fact that a strong aliphatic acid solution with hydrogen peroxide exists in equilibrium with the corresponding organic peracid.

$$\overset{O}{\underset{\|}{RC}}-OH + H_2O_2 \rightleftharpoons \overset{O}{\underset{\|}{RC}}-OOH + H_2O$$

However, in the absence of a strong acid catalyst, such as a mineral acid, the attainment of equilibrium is impractically slow, especially at temperatures below 40° C. At higher temperatures, it is difficult to prevent the excessive loss of active oxygen unless the oxidizable organic substance is also present to react with the organic peracid as it forms. For this reason, it is common practice, whenever possible, to employ hydrogen peroxide under conditions for the in situ formation of the organic peracid at temperatures ranging up to the boiling point of the aliphatic acid.

The peracid formed in situ can be reacted with an olefinic material to produce an epoxy (oxirane) compound as a primary product.

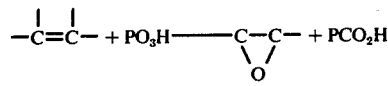

The reaction is, of course, two-staged, since the peracid must be formed first.

Common organic peracid systems include glacial acetic acid or formic acid with hydrogen peroxide. The organic peracids thus formed are unstable and considered a hazard particularly when the organic peracid is relatively concentrated.

It is known that the mild oxidizing action of hydrogen peroxide is increased considerably by use of certain metallic catalysts. One example of metallic catalyst is ferrous sulfate which is employed in a redox system:

$$FE^{++} \rightarrow Fe^{+++}$$

It has been employed with hydrogen peroxide and is generally known as Fenton's Reagent. Other catalyst include osmium and tungstic oxides employed to hydroxylate aromatic and unsaturated hydrocarbons and to effect other oxidations. These additional catalysts are classed as Milas' Reagents which together with Fenton's Reagent constitute the bulk of the metal activated hydrogen peroxide systems. Hydrogen peroxide in metal-activated systems reacts as though it was dissociating into two hydroxyl radicals.

Fenton's oxidations are, in fact, believed to proceed through the intermediate formation of hydroxyl free radicals:

$$Fe^{+++}H_2O_2 \rightarrow Fe^{+++}+OH^-+OH$$

The $Fe^{++}$—$F^{+++}$ systems, and such other redox systems as $Cu^+$—$Cu^{++}$, are normally employed with hydrogen peroxide in aqueous acid medium. A small amount of sulfuric acid is added to an aqueous solution of ferrous sulfate heptahydrate so that Fenton's oxidations are carried out at a pH of 1–4. In a less acid solution, the reaction efficiency is decreased, and hydrogen peroxide is catalytically decomposed.

Other metal-activated systems include in decreasing order of catalytic efficiency the following:

$$O_x, O_4, WO_3, MoO_3, SeO_2, CrO_3, V_2O_5, TiO_2 \text{ and } Ta_2O_x$$

Derivatives of the aforementioned catalyst, such as phosphotungstic acids (e.g. $H_3PO_412WO_3$) are also effective as catalysts for hydrogen peroxide.

The prior art shows four general methods of incorporating the peroxide bond (—OO—) into organic molecules. These methods include auto-oxidation, ozonization, the association of oxygenated free radicals, and the addition and substitution reactions of hydrogen peroxide and hydroperoxides. Typically, hydrogen peroxide is reacted with acids, anhydrides, esters, alcohols, organic sulfates and sulfonates, carbonyl compounds, and organic chlorine compounds to produce organic peroxides.

The reaction of acids anhydrides and esters with hydrogen peroxide ordinarily lead to the formation or organic peracids, although other organic percompounds may result. The most polular method of preparing a peracid is by mixing hydrogen peroxide and an aliphatic acid in the presence of a strong acid catalyst such as sulfuric acid. Typically an equimolar mixture of high strength hydrogen peroxide and acetic acid with one percent sulfuric acid catalyst reaches equilibrium after standing for 12 to 16 hours.

The resin techinque for peracetic acid formation is considered much faster and permits continuous or batchwise preparation.

The resin technique or peracetic acid formation is operated simply by passing a mixture of glacial acetic acid and hydrogen peroxide through a cation exchange resin column. The column contains polystyrene sulfonic acid resin which has been treated with glacial acetic acid to remove excess water. Under conditions for operation of the resin technique, a contact time of 12 to 16 minutes of about 45° C is sufficient for maximum conversion of hydrogen peroxide to operacetic acid. The serious drawback in this method is that it requires high strength hydrogen peroxide and thus creates a serious hazard.

A common procedure for converting an alcohol, R—O—H, to a hydroperoxide, R—OOH, consists of reacting hydrogen peroxide and tertiary alcohols is strong sulfuric acid. The reaction is believed to involve the formation of an intermediate sulfate and, therefore, is similar to the alkylation of hydrogen peroxide by dialkyl sulfates. The reaction often results in serious explosions, although the final products of such reactions are relatively stable. Prior art methods do not produce peroxide products with primary or secondary alcohols very easily. Mixtures of a tertiary alcohol and hydrogen peroxide have been used as germicides, fungicides, bleaching agents, and peroxide reagents.

The strong sulfuric acid used in the hydrogen peroxide-alcohol reaction is sometimes replaced by heteropolyacids having multiple inorganic acid radicals. The heteropolyacids which are soluble in ether, contain the elements of phosphorous, silicon, or boron, coordinated with a metallic oxide such as tungsten oxide. The characteristic solubility of heteropolyacids allows the preparation of alkyl hydroperoxides to be carried out in ether.

The known methods of converting carbinols of many types to hydroperoxides and disubstituted peroxides makes use of strong sulfuric acid as a catalyst. Typically, acetylene peroxides are formed by the interaction of hydrogen peroxide and the hydroxyl group of acetylenic carbinols in the presence of strong sulfuric acid. The peroxides thus formed are unusually stable despite the presence of the acetylenic bond.

Dialkyl sulfates and alkyl hydrogen sulfates can be used to produce hydroperoxides and dialkyl peroxides by a reaction with alkaline hydrogen peroxide. These peroxides are often used as polymerization catalysts and diesel fuel additives. Typically, primary and secondary dialkyl peroxides are prepared by the alkylation of hydrogen peroxide with alkyl methane sulfonates in liquid alkaline methanolic solution. A known method for producing sodium peroxy sulfonates is carried out by reacting a sulfonic acid such as naphthalene sulfonic acid and sodium peroxide in a liquid medium. The operation is conducted in a cold environment to reduce the violence of the reaction. The peroxy product obtained has aproximately 6% active oxygen and is considered useful as a bleaching agent or insecticide.

Olefins have been transformed to hydroperoxides in a reaction which amounts to the addition of hydrogen peroxide to the double bond. The reaction, however, is conducted in strong sulfuric acid according to known methods and probably involves the formation of an intermediate sulfate.

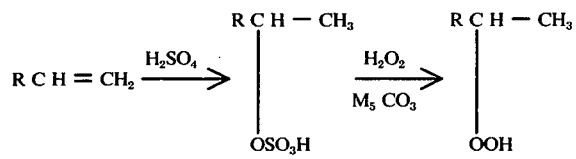

The preparation typically takes place at below 0° C and takes several hours.

It is known that hydrogen peroxide can be reacted with an aldehyde of a ketone in the presence of a catalyst to form a peroxide compound. The following equilibrium is believed to occur for an aldehyde and hydrogen peroxide:

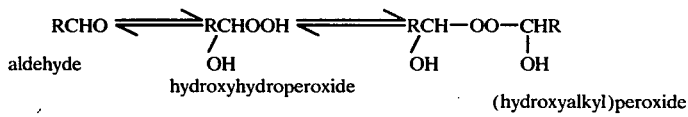

Typically, formaldehyde is treated with hydrogen peroxide in ether in the presence of $P_2O_5$. The peroxide product is very explosive. Both cyclic ketones and aliphatic ketones have a tendency to form stable but hazardous peroxides. As a rule, known methods produce unstable peroxides of aromatic ketones and aromatic aldehydes because of the greater ease of migration of the phenyl radicals attached to the carbonyl carbon.

It is known that organic peroxides can be formed by reacting hydrogen peroxide with organic chlorine compounds. The reaction is generally conducted in the presence of a chlorine acceptor which may be caustic or organic bases such as pyridine.

SUMMARY OF THE INVENTION

One of the principal objects of the invention is to provide a peroxide compound comprising the steps of preparing a reactive aluminum and reacting the reactive aluminum with a liquid mixture of hydrogen peroxide and an organic compond. Another object of the present invention is to provide a method for forming a metallic-organoperoxide comprising the steps of forming a reactive aluminum and contacting a liquid mixture of hydrogen peroxide and an organic compound with the reactive aluminum. Another object of the invention is to provide a method for forming an organometallic-peroxide comprising the steps of forming a reactive aluminum and contacting a liquid mixture of hydrogen peroxide and an organic compound with the reactive aluminum.

Another object of the present invention is to provide a method of forming an alcohol peroxide comprising the steps of forming a reactive aluminum and contacting a liquid mixture of an alcohol and hydrogen peroxide with the reactive aluminum.

Another object of the invention is to provide a method of forming an aldehyde peroxide comprising the steps of forming a reaction aluminum and containing a liquid mixture of an aldehyde and hydrogen peroxide with the reactive aluminum.

Another object of the invention is to provide a method of forming a ketone peroxide comprising the steps of forming a reactive aluminum and contacting a liquid mixture of a ketone and hydrogen peroxide with the reactive aluminum.

The invention accordingly comprises the several steps and the relation of one or more of such steps with respect to each of the others, or as exemplified in the following detailed disclosure, and the scope of the applicaton of which will be indicated in the claims.

THE INVENTION

The present invention is focused on the utilization of the catalytic properties of a reactive aluminum prepared by the methods described in co-pending patent application, "Catalytic Electrode", Ser. No. 211,979, filed Dec. 27, 1971, now abandoned.

The reactive aluminum in the present disclosure corresponds to the aluminum catalytic electrode described in the aforementioned patent application.

Generally, a reactive aluminum is prepared by contacting highly pure aluminum in the presence of a hydrogen ion source with a metal which can form a hydride. The hydrogen ion source can be inorganic acid or the like or an inorganic acid such as citric acid or acetic acid or the like. The reactive aluminum in an alkali solution such as water and sodium hydroxide will serve as a hydrogen ion source for the formation of another reactive aluminum.

The metal for forming the reactive aluminum can be an element or an alloy. Preferably, the metal is gallium, or indium or an alloy of the two or mercury. A desirable characteristic of the metal is that it is soft and pliable and preferably a liquid during the process in order to permit the rapid permeation through the aluminum. The general rule is that an element with an atomic volume near that of hydrogen is preferred for this metal.

It should be understood that the term "highly pure" herein means greater than 99% and that purities in the order of 99.9 and 99.99% are preferable.

One simple method of preparing a reactive aluminum is to use an aluminum piece, such as a rod 99.99% pure having a length of 3 inches and a diameter of a half inch. The aluminum rod is placed on its side in a glass dish and sufficient 2N acid, such as hydrochloric acid, is added to cover the aluminum rod. The aluminum rod is contacted with the metal such as mercury or gallium and the metal is given time to permeate through the aluminum rod. Of course, the aluminum rod can be treated in a vertical position if desired and a rod shape is not necessary. Other shapes may be used.

The concentration of the acid can cover the broadest range to even includde neutral water. The choice of the hydrogen ion source such as an acid will depend upon the peroxide compound to be formed and the concern over impurities.

It is preferable to prepare the aluminum rod for the reaction by at least partially stripping the aluminum oxide coating which has formed on the surface due to the exposure to air and moisture. If the aluminum rod has been stripped, then hot water can serve as the hydrogen ion source. Otherwise, it may be desirable to start out with an acid to strip off the oxide coating on the aluminum rod in order to initiate the reaction to form the reactive aluminum as quickly as possible. Of course, the aluminum rod may be striped mechanically with sandpaper of a file or the like.

The inter-reaction which occurs between the aluminum rod and the acid, gives rise at the start to the formation of large bubbles which rise up to the surface through the acid. After a while it will be observed that instead of large bubbles forming at the top of the aluminum rod and then breaking free and rising to the surface of the acid, tiny bubbles will be eminating from many parts of the upper surface of the aluminum rod. The occurrence of the multitude of tiny bubbles indicates that the aluminum rod is being converted into a "reactive" aluminum.

Generally, the aluminum rod will take up or absorb from 0.1 to 5 percent of the mercury by weight depending upon how long the reaction is permitted to continue. A range of 2 to 3 percent of the mercury by weight is desired for many applications. However, in some applications as little as 0.1 percent of the mercury by weight is preferred.

The reaction can be stopped on the basis of the increased weight of the aluminum rod due to the absorption of the metal or due to the production of a multitude of tiny bubbles for a period of 10 to 15 minutes or due to the observance of the hydrolysis of water when the aluminum rod being treated is placed therein.

An aluminum rod treated as described, displays surprisingly active catalytic properties not at all suggested by the prior art. The prior art has recognized that aluminum and an amalgam of aluminum exhibit catalytic properties. It is of considerable significance that the treatment of highly pure aluminum as described herein exhibits catalytic and initiating properties that far exceed prior art contemplation.

Another method of preparing a reactive aluminum uses gallium instead of mercury. The same aluminum rod is placed in a glass dish and covered with hydrochloric acid and one end of the aluminum rod is contacted with the gallium having a mass from 1 to 3 percent of the aluminum rod. The treatment takes from 10 to 15 minutes depending upon how well the oxide coating on the aluminum rod has been removed at the point of contact of the gallium and the aluminum rod. A fairly clean part of the aluminum rod is indicated by the observance of large bubbles generated thereat.

It is desirable to dip a reactive aluminum formed with gallium into anhydrous alcohol immediately after completion of the process in order to prevent the formation of a brownish compound on the aluminum rod thereafter.

The amount of the metal in the aluminum rod can be varied in accordance with applications. In general, if a high percent of the metal by weight is desired, quick cooling of the reactive aluminum rod after formation will prevent the squeezing out of the metal due to an exothermic reaction. Water is convenient for this purpose for a reactive aluminum formed with mercury. However, in cases where it is desired to reduce the amount of, say, mercury from several percent by weight to, say, 0.1% by weight, the reactive aluminum can be heated to squeeze out the mercury.

From the above, it is clear herein, including the claims, what is meant by a "reactive aluminum".

The reactive aluminum exhibits an aligned matrix and, it is believed, capable of converting at least partially to a hydride at one or more valences and produces $Al^{+++}, e^-, H+, OH^-, HO_2^{--}$, and $O^{--}$ radicals depending upon the fluid contacting the reactive aluminum. Where the fluid is hydrogen peroxide, it is believed that $O_2^-$ and $O_2^{--}$ radicals are produced in addition to the aforementioned radicals.

Certain impurities such as copper and iron, inhibit the formation of a reactive aluminum and so should be avoided in the aluminum rod. Impurities which inhibit or promote the reaction are given in the aforementioned catalytic electrode application.

An important aspect of the present is the realization that the aforementioned treatment of highly pure aluminum results in a reactive aluminum which can bring about a reaction with an organic compound and hydrogen peroxide to form a peroxide compound. The reactive aluminum not only brings about the formation of the peroxide compound, but further results in the aluminum from the reactive aluminum entering into the peroxide compound to form a part thereof. The amount of aluminum which forms a part of the peroxide compound can vary from a fraction of a percent to 5 percent or more.

Generally, the reaction time for the production for most of the peroxides in accordance with the present invention is considerably shorter than the time taken by prior art methods. The rate of the reaction for the production of a peroxide in accordance with the present method will be determined by well known parameters, such as the concentration of the hydrogen peroxide, the temperature of the constituents, the quantity of the reactive aluminum, and other factors.

If a reaction is permitted to proceed too rapidly so that the exothermic reaction elevates the temperature of the constituents, there is a possibility that the hydrogen peroxide will tend to break up into water and oxygen and thereby reduce the concentration of the hydrogen peroxide. As a result, there will be fewer peroxide groups available for the formation of the desired peroxide compound.

One approach for controlling the reaction rate is to add the hydrogen peroxide a little at a time. Of course, this presumes the presence of a liquid organic compound already present in order to form the mixture with the hydrogen peroxide.

Of course, a dilute hydrogen peroxide can be used in order to reduce the exothermic reaction to produce a relatively low-grade peroxide compound without the incidence of an elevated temperature or a reaction which requires some monitoring.

Generally, the atomic bonding in an organic peroxide formed by the present methods will be dependent upon the bonding that is present in the organic compound used in the reaction with hydrogen peroxide in the presence of the reactive aluminum. For example, it is well known that double bonds in organic compounds tend to be preferred sites for inter-reaction or reactions in general.

Generally, an organic compond having only single bonds can be reacted with hydrogen peroxide in the presence of the reactive aluminum to form an organic peroxide which shows hydroperoxide groups attached to the aluminum atoms with the organic groups coordinated about the aluminum atom. The precise structure or organization is not known. In practicing the present method to form an organic peroxide with an organic compound having single bonds, it is preferred to use a relatively dilute solution of hydrogen peroxide so as to provide a readily available source of hydroxyl radicals. A water solution of hydrogen peroxide between 3 to about 10% is preferable. Higher concentrations of hydrogen peroxide can be used but will tend to produce an inorganic peroxide in competition with the formation of the organic-metallic-peroxide described. The examples given herein illustrate the use of single bonded organic compounds such as alcohols, ketones, and aldehydes.

In the case where the organic compounds include other than single bonds such as double bonds, triple bonds, multiple bonds in general, or the like, an organic peroxide having a peroxide or hydroperoxide group attached directly to an organic group can be produced. Since the organic peroxide product in this case also includes an aluminum atom, it is proper to describe such products as a metallic-organic-peroxides.

The presence of a ring structure in the organic compounds does not hereto affect the formation of an organic peroxide by the present methods. The organic compounds having at least one multiple bond include, the so-called vinyl-type compound. Basically, a vinyl-type compound is characterized by the formula

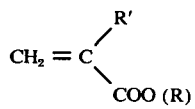

The R or R' can be a member of the aliphatic series. When a nitrile group replaces the carboxyl group then acrylonitrile is obtained. For an amide group acrylamide is obtained while for a aldehyde group acrolein or acrylaldehyde is obtained. Either the R or R' or both can be replaced by an halide or an active halide.

It is interesting to note that in the article entitled, "Thermochemistry of the Hydrogen Polyoxides $H_2O_3$ and $H_2O_4$" by Paul A. Giguère, published in the Transactions New York Academy of Sciences, that the presence of three radicals of $H_2O_3$ and $H_2O_4$ were prepared and measured under the extreme conditions of temperature of less than 100° K. Furthermore, this article reports to indicates that the formation of higher order hydrogen polyoxides are extremely difficult and require extreme temperature and pressure requirements. Although no limitation is intended to be suggested by the presentation of theories related to the operation of the present invention, it is believed that in carrying out the present invention there is a considerable production of radicals of $H_2O_3^{--}$ and $H_2O_4^{--}$ due to the reactive aluminum reacting with the hydrogen peroxide. It has been observed that during the formation of an organic peroxide by the method of the present invention the removal of the reactive aluminum from the mixture into air produced a red meruric oxide on the reactive aluminum which had been prepared with mercury. The formation of red mercuric oxide rather than black mercuric oxide is an indication of $O_2^-$ radicals which points to the aforementioned polyoxide radicals.

In another experiment, part of an organic peroxide prepared with a carboxylic acid, was contacted with some mercury and immediately produced red mercuric oxide which for the same reason given previously, tends to confirm the proposed theory.

The production of higher order polyoxide radicals is favored by the use of highly concentrated hydrogen peroxide in the order of 50% and the use of elevated temperatures above 50° C. There is the possibility that the use of highly concentrated hydrogen peroxide at an elevated temperature may tend to cause a very quick breakdown of the hydrogen peroxide so that the reaction carried out at an elevated temperature will tend to readily reduce the concentration of the hydrogen peroxide.

An interesting theory has been evolved to explain the formation of organic peroxides in terms of the present methods. The theory is not intended to be a limitation. To start with, in a typical reaction involving hydrogen peroxide with a carboxylic acid, the carboxylic acid which is represented as RCOOH forms a layer around the reactive aluminum rod and the hydrogen peroxide forms a layer on the layer of the carboxylic acid. A layer of the carboxylic acid then forms about the hydrogen peroxide layer and it continues alternating between the two types of layers. This can be shown diagrammatically by the following:

TABLE 1

| RCOO H | RCOO H | RCOO | H |
| OH H O | OH H O | OH | H O |
| RC OOH | RC OOH | RC OO H | |
| OH H O | OH H O | OH H O | |
| RCOO H | RCOO H | RC OO | H |
| OH H O | OH H O | OH | H O |

In accordance with the hypothesis given herein, Table 1 shows the arrangement of the layers of carboxylic acid and hydrogen peroxide alternating and having an atomic arrangement corresponding with the charges of the atoms present therein. The cells shown in Table 1 indicate the cooperation between atoms to produce radicals which will eventually combine with aluminum atoms to form the metallic-organo-peroxide. It is seen that the radical RCOOOH is formed while hydrogen atoms which break away from the carboxylic acid atoms combine with hydroxyl atoms from the hydrogen peroxide to produce water. The hydrogen atoms readily diffuse about and through the matrix of the reactive aluminum to interact therein and ultimately the formation of the aluminum carboxylic peroxide takes the form of

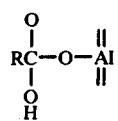

It is believed that the unusual stability of the organic peroxides prepared in accordance with the present methods is due to the fact that if the oxygen atom between the carbon and aluminum atoms is dislodged, the aluminum atom will immediately couple over to the carbon atom to restore the stability of the atomic structure. In the proposed form, it is noted that the aluminum atom acts as a cross-link between the organic peroxide groups.

Highly concentrated hydrogen peroxide has a tendency to produce hydroperoxy groups which are relatively stable radicals as compared to other peroxide type radicals. The hypothesis for the interreaction between a carboxylic acid and a weak hydrogen peroxide solution equals a somewhat similar hypothesis as given above in that alternate layers are produced on the reactive aluminum but the pattern is as shown in Table 2:

| RCOO H | RCOO H | RCO O H |
| H O O | H O O | HOO O |
| RC OO H | RCOOH | RCOO H |
| H O O | H O O | H O O |
| RCOO H | RCOO H | RCOO H |
| H O O | H O O | H O O |

As can be seen, the layers of the carboxylic acid alternate with hydroperoxy radicals. The organization of the atoms with respect to each other is based on the supposed interreaction between the charges carried by the various radicals. The cells indicated in Table 2 suggest how the various atoms and radicals interreact in order to bring about the formation of the aluminum carboxylic peroxide. The presence of the hydroperoxide groups tends to give rise to hydroxyl atoms as the desired product is being formed. It is believed that the hydrogen radicals diffuse into the reactive aluminum. It may be that the overall reaction which occurs for hydrogen peroxide and a carboxylic acid is some combination of the illustrated reaction formats given in Tables 1 and 2. Furthermore, it may be that the resulting organic peroxide contains hydroperoxide groups.

It is of interest that generally peroxide is the preferred reactant but the essential features for the production of organic peroxide rely only on the presence of O⁻ radicals or the like. Known methods of producing the desired radicals include, for example, the use of ultraviolet light on a mixture containing water to produce $O_3^-$ radicals. Another way of getting the desired radicals is to generate ozone and bubble it through the mixture which will be used to produce the organic peroxide. Other equivalent means for providing the desired radicals will be obvious to those skilled in the art.

The use of hydrogen peroxide with the concentration of about 30% is convenient and the examples given herein were performed using hydrogen peroxide with a 30% concentration except where indicated differently. Also, most experiments carried out were done at a temperature below 50° C, but, of course, as it has been noted, it is sometimes desirable to use an elevated temperature in order to increase the occurrence of peroxide radicals. As noted previously, organic peroxides have many known uses. The present organic peroxides provide a novel use as a catalyst for the formation of resins since it is possible to use an organic peroxide of the same organic radical corresponding to the main organic radical in the resin. This is an attractive use since no problem of removing the catalyst occurs since the catalyst becomes an integral and tolerable component in the resin formed thereby.

EXAMPLES

Illustrative, non-limiting examples of the practice of the invention are set out below. Numerous other examples can readily be evolved in the light of the guiding principles and teachings contained herein. The examples are intended merely to illustrate the invention and not in any sense to limit the manner in which the invention can be practiced. The parts and percentages recited therein and all through this specification, unless specifically provided otherwise, refers to parts by weight and percentages by weight.

EXAMPLE 1

An aluminum methyl acrylic peroxide is formed by combining 86 grams of methyl acrylate and 393 grams of water, reacting with a reactive aluminum rod of about 54 grams, and then adding gradually about 40 grams of hydrogen peroxide.

EXAMPLE 1

An aluminum ethyl oxalate peroxide is formed by combing 146 grams of ethyl oxalate, reacting with a reactive aluminum rod of about 54 grams, and then gradually adding about 100 grams of hydrogen peroxide.

EXAMPLE 3

An aluminum vinyl acetic peroxide is formed by combining 86 grams of vinyl acetate, reacting with a reactive aluminum rod of about 54 grams, and then gradually adding about 80 grams of hydrogen peroxide.

EXAMPLE 4

An aluminum ethyl alcohol peroxide is formed by combining 44 grams of ethyl alcohol and 40 grams of hydrogen peroxide and reacting with a reactive aluminum rod of about 50 grams. The hydrogen peroxide should be added gradually and should have a concentration of less than 10%.

EXAMPLE 5

An aluminum methyl ethyl ketone peroxide is formed by combining 100 grams of methyl ethyl ketone with 100 grams of hydrogen peroxide and reacting with a reactive aluminum rod of about 100 grams. The hydrogen peroxide should be added gradually and have a concentration of 10% or less.

EXAMPLE 6

An aluminum butyl alcohol peroxide is formed by combining 74 grams of butyl alcohol with about 100 grams of hydrogen peroxide and reacting with a reactive aluminum rod of about 100 grams. The hydrogen peroxide should be added gradually and have a concentration of 10% or less.

EXAMPLE 7

An aluminum acetaldehyde peroxide is formed by combining 44 grams of acetaldehyde with 50 grams of hydrogen peroxide and reacting with a reactive aluminum rod of about 50 grams and having a concentration of 10% or less.

EXAMPLE 8

An aluminum acetone peroxide is formed by combining 58 grams of acetone with 100 grams of hydrogen peroxide and reacting with a reactive aluminum rod of about 50 grams.

EXAMPLE 9

An aluminum isopropyl alcohol peroxide is formed by reacting 100 grams of isopropyl alcohol and 150 grams of hydrogen peroxide with a reactive aluminum rod of about 100 grams. The hydrogen peroxide should have a concentration of 10% or less.

Having thus described the invention, what I claim as new and desired to be secured by Letters Patent, is as follows:

1. A method of forming a peroxy compound which comprises contacting and reacting:
   a. reactive aluminum comprising highly pure aluminum permeated with a metal having an atomic volume close to hydrogen; with
   b. a liquid mixture of
      i. hydrogen peroxide; and
      ii. a member selected from alcohols, ketones, and aldehydes; and
   separating the peroxy compound from unreacted reactive aluminum.

2. The method of claim 1 wherein said metal having an atomic volume close to hydrogen is a liquid metal selected from mercury, gallium and indium/gallium alloys.

3. The method of claim 1 wherein said highly pure aluminum has a purity of at least 99.99% by weight.

4. The method of claim 1 wherein said reactive aluminum is prepared by contacting highly pure aluminum with a liquid metal selected from mercury, gallium and indium/gallium alloys in the presence of a hydrogen ion source so as to permeate said liquid metal through said aluminum.

5. The method of claim 1 wherein member (ii) is an alcohol.

6. The method of claim 5 wherein said alcohol is ethyl alcohol.

7. The method of claim 5 wherein said alcohol is butyl alcohol.

8. The method of claim 5 wherein said alcohol is isopropyl alcohol.

9. The method of claim 5 wherein the concentration of hydrogen peroxide in liquid mixture (b) is up to 10% by weight.

10. The method of claim 1 wherein member (ii) is a ketone.

11. The method of claim 10 wherein said ketone is acetone.

12. The method of claim 10 wherein said ketone is methylethylketone.

13. The method of claim 10 wherein the concentration of hydrogen peroxide in liquid mixture (b) is up to 10% by weight.

14. The method of claim 1 wherein member (ii) is an aldehyde.

15. The method of claim 14 wherein said aldehyde is acetaldehyde.

16. A method of forming a peroxy compound which comprises the steps of:
   a. contacting aluminum having a purity of at least 99.99% by weight, in the presence of a hydrogen ion source, with a liquid metal selected from mercury, gallium and indium/gallium alloys to permeate said liquid metal through said aluminum and prepare a reactive aluminum;
   b. contacting and reacting said reactive aluminum with a mixture of:
      i. hydrogen peroxide; and
      ii. a member selected from alcohols, ketones, and aldehydes; and
   c. separating the peroxy compound from unreacted reactive aluminum.

17. A peroxy compound prepared by contacting and reacting:

a. a reactive aluminum comprising highly pure aluminum permeated with a liquid metal selected from mercury, gallium and indium/gallium alloys; with
b. a liquid mixture of
  i. hydrogen peroxide; and
  ii. a member selected from alcohols, ketones, and aldehydes.

18. The peroxy compound of claim 17 wherein said highly pure aluminum has a purity of at least 99.99% by weight.

19. A method of forming a peroxy compound which comprises contacting and reacting:
  a. a reactive aluminum comprising highly pure aluminum permeated with a liquid metal selected from mercury, gallium and indium/gallium alloys; with
  b. a liquid mixture of
    i. hydrogen peroxide; and
    ii. a member selected from methyl acrylate, ethyl oxalate, ethyl alcohol, isopropyl alcohol, butyl alcohol, acetone, methyl ethyl ketone and acetaldehyde; and
separating the peroxy compound from unreacted reactive aluminum.

20. A method of forming a peroxy compound which comprises the steps of:
  a. contacting aluminum having a plurality of at least 99.99% by weight, in the presence of a hydrogen ion source, with a liquid metal selected from mercury, gallium and indium/gallium alloys to permeate said liquid metal through said aluminum and prepare a reactive aluminum;
  b. contacting and reacting said reactive aluminum with a mixture of
    i. hydrogen peroxide; and
    ii. a member selected from methyl acrylate, ethyl oxalate, ethyl alcohol, isopropyl alcohol, butyl alcohol, acetone, methyl ethyl ketone and acetaldehyde; and
  c. separating the peroxy compound from unreacted reactive aluminum.

21. A peroxy compound prepared by contacting and reacting:
  a. a reactive aluminum comprising highly pure aluminum permeated with a liquid metal selected from mercury, gallium and indium/gallium alloys; and
  b. a liquid mixture of
    i. hydrogen peroxide; and
    ii. a member selected from methyl acrylate, ethyl oxalate, ethyl alcohol, isopropyl alcohol, butyl alcohol, acetone, methyl ethyl ketone and acetaldehyde.

* * * * *

UNITED STATES PATENT OFFICE
CERTIFICATE OF CORRECTION

Patent No. 4017527       Dated Apr. 12, 1977

Inventor(s) George G. Merkl

It is certified that error appears in the above-identified patent and that said Letters Patent are hereby corrected as shown below:

Column 2, line 27, formula should read therefor --
$Fe^{++} + H_2O_2 \rightarrow Fe^{+++} + OH^- + OH$ --;

Column 9, Table 1 was incorrectly spaced, should read therefor

--;

Column 10, Table 2 was incorrectly spaced, should read therefor

--

Signed and Sealed this

Fourth Day of October 1977

[SEAL]

Attest:

RUTH C. MASON       LUTRELLE F. PARKER
*Attesting Officer*      *Acting Commissioner of Patents and Trademarks*